United States Patent [19]

Guggenberger et al.

[11] Patent Number: 5,569,691

[45] Date of Patent: Oct. 29, 1996

[54] HYDROPHILIZED POLYETHERS

[75] Inventors: Rainer Guggenberger, Herrsching; Erich Wanek, Kaufering; Oswald Gasser, Seefeld, all of Germany

[73] Assignee: Thera Patent GmbH & Co. KG Gesellschaft fur Industrielle Schutzrechte, Seefeld, Germany

[21] Appl. No.: 206,853

[22] Filed: Mar. 7, 1994

[30] Foreign Application Priority Data

Mar. 5, 1993 [DE] Germany .................. 43 06 997.5

[51] Int. Cl.$^6$ ........................................... C08K 5/24
[52] U.S. Cl. .................. 524/261; 524/265; 524/366; 524/378; 524/462; 524/463; 524/588
[58] Field of Search ............................ 524/261, 265, 524/366, 378, 462, 463, 588

[56] References Cited

U.S. PATENT DOCUMENTS

| | | | |
|---|---|---|---|
| 3,453,242 | 7/1969 | Schmitt et al. ............... | 260/77.5 |
| 3,505,377 | 7/1970 | Morehouse et al. . | |
| 3,980,688 | 9/1976 | Litteral et al. . | |
| 4,160,776 | 7/1979 | Scardera et al. . | |
| 4,167,618 | 9/1979 | Schmitt et al. . | |
| 4,226,794 | 10/1980 | Scardera et al. . | |
| 4,337,168 | 6/1982 | Scardera et al. . | |
| 4,431,789 | 2/1984 | Okazaki et al. . | |
| 4,532,268 | 7/1985 | Jochum et al. . | |
| 4,657,959 | 4/1987 | Bryan et al. ............... | 524/266 |
| 5,130,348 | 7/1992 | Zahler et al. ............... | 523/109 |

FOREIGN PATENT DOCUMENTS

| | | |
|---|---|---|
| 0110429 | 6/1984 | European Pat. Off. . |
| 0173085 | 3/1986 | European Pat. Off. . |
| 0173085 | 3/1986 | European Pat. Off. . |
| 0366977 | 5/1990 | European Pat. Off. . |
| 0421371 | 4/1991 | European Pat. Off. . |
| 0480238 | 4/1992 | European Pat. Off. . |
| 2515593 | 10/1975 | Germany . |
| 3246654 | 12/1982 | Germany . |
| 1745810 | 6/1984 | Germany . |
| 3728216 | 8/1987 | Germany . |
| 3805482 | 2/1988 | Germany . |
| 3741575 | 6/1988 | Germany . |
| 4010281 | 3/1990 | Germany . |
| 3838587 | 5/1990 | Germany . |
| 4019249 | 6/1990 | Germany . |
| 4119484 | 12/1992 | Germany . |
| 4293955 | 10/1992 | Japan . |
| 1745738 | 10/1989 | U.S.S.R. . |

OTHER PUBLICATIONS

Noll, Walter. *Chemistry and Technology of Silicones.* 447–452.
Gribi, Quintessenz, Zahntech. pp. 1262–1274, 1992.
Barder & Setz. *Wettability and Reproduction Accuracy of Modelling Compositions.* Dtsch. Zahndrztl. Z. 46, p. 346–348, 1991.
Polyethers Part I, Norman G. Gaylord, ed., pp. 147–150.
Polyethers Part I, Norman G. Gaylord, ed., pp. 231–237.
Bernard Parant, Index—The Non–Ionic Surfactants (1988).
Bartholome, et al., Ullmanns Encyklopadie der technischen Chemie, Band 22, vol. 4, (1922) pp. 488–496.
Silwet Surfactants, (1988) pp. 1–20.
Ucon Fluids & Lubricants (1955) Table of Contents.
Phillps, Ralph W., Skinner's Science of Dental Materials, 7th ed., 1973, p. 141.
Encyclopedia of Polymer Science and Engineering, Supplement Volume, Acid–Base Interactions to Vinyl Chloride Polymers, 1989, pp. 570–573.
Ullman's Encyclopedia of Industrial Chemistry, 5th Ed., vol. A24, pp. 65–66 and 69.
Brown, David, *Journal of Dentistry*, vol. 1, pp. 265–274.

*Primary Examiner*—Edward Cain
*Attorney, Agent, or Firm*—Birch, Stewart Kolasch & Birch, LLP

[57] ABSTRACT

The invention relates to a rubber-elastic composition which comprises a polyether material, and which in the completely vulcanized and completely polymerized form, contain 0.1 to 15 wt. %, relative to the total weight of the composition, of at least one hydrophilic nature imparting agent selecting from the group consisting of a hydrophilic silicone oil having one or more siloxane groups as a hydrophobic part and one or more ether groups as a hydrophilic part, a fluorinated hydro-carbon, a block copolymer of ethylene oxide/propylene oxide, a fatty alcohol derivative, an alkyl phenol derivative, a fatty amine, an amine oxide, a fatty acid glycol and glycerin derivative, a fatty acid, and a fatty acid monoester. The composition is suitable as dental impression composition and has, in the completely polymerized state, even with multiple disinfections in an aqueous disinfecting solution, a continuing good ability to flow on (small wetting angle) and an unchanged dimensional stability.

15 Claims, No Drawings

HYDROPHILIZED POLYETHERS

FIELD OF THE INVENTION

The present invention relates to hydrophilized rubber-elastic impression and doubling compositions based on vulcanizable polyether materials which are used in particular in the dental field, but also in orthopaedics, and to a process for their production and to a suitable agent for forming an impression molding. The present invention relates in particular to vulcanizable polyether pastes with aziridino end-groups, addition crosslinking polyether silicone pastes having H—Si groups and radically vulcanizable polyether acrylate and methacrylate pastes for the production of precise impressions of toothed, partially toothed and untoothed jaws and of plaster models.

BACKGROUND OF THE INVENTION

Compositions are known and offered in different viscosity classes for different impression methods. For example, known compositions include kneadable and highly-viscous compositions which are for spoon application, and medium- and low-viscosity compositions which are preferably for spray application.

DE-B-17 45 810 provides impression compositions of polyether materials with aziridino end-groups.

DE-A1-37 41 575 and DE-A1-38 38 587 provide impression compositions based on polyether materials with alkenyl groups and polyorganosiloxane radicals, containing H—Si groups, which polymerize under the action of platinum catalysts.

EP-A2-0 173 085 provides impression compositions of polyether materials with acrylate and methacrylate groups which polymerize after irradiation with light of a suitable wavelength—initiated by the decomposition of a photo initiator.

The above polyether materials have a good ability to flow on hydrophilic oral surfaces and therefore a higher impression exactness can be obtained with these materials than with other known impression compositions, e.g., those based on conventional hydrophobic silicones. However, a disadvantage of these known polyether materials is that their water absorption is high when compared with silicone impression compositions. In this regard, the disinfection of impression compositions by means of aqueous disinfection baths is now indispensable and is frequently even repeated, in order to break the chain of infection. As a result, there has been an increased importance placed on achieving the smallest water absorption possible, as well as small swelling and therefore small changes in dimension.

Another disadvantage of the known polyether materials is their greater wetting angle compared with other known impression compositions, e.g., those based on hydrocolloids. The latter of these show a poor dimensional stability when compared with polyether materials. As a result of their high susceptibility towards swelling or shrinking, the hydrocolloids are not storage-stable, and impressions made therewith have to be cast immediately.

A larger wetting angle can lead to reduced flow and to the persistence of air inclusions when casting the impression with a plaster suspension. As a result plaster models of this type are unusable. The wetting angle is the angle which the edge of a water drop forms relative to the substrate surface (Walter Noll, Chemistry and Technology of Silicones, Academic Press, 1968, particularly pages 447–452).

Other known silicone impression compositions have the advantage of a relatively small water absorption, but their ability to flow on their wetting angles are not satisfactory. Attempts have therefore been made to confer a hydrophilic character upon these silicone compositions by incorporating a hydrophilizing agent and to reduce their wetting angle. Such compositions are for example described in EP-A1-0 480 238. A major disadvantage of the hydrophilized silicone compositions is, however, that the small wetting angle achieved through the addition of the hydrophilizing agent is to a very large extent lost even by a single disinfection in an aqueous disinfection bath.

The increased water absorption of hydrophilic silicones, which is many times that of the non-hydrophilized silicones, is particularly disadvantageous. Gribi, Quintessenz, Zahntech. 18, 1261–1274 (1992) describes in FIG. 7, page 1271 specimens of the same size which were exposed to flowing or standing water for 8 hours. After surface drying, the specimens were weighed. As a result it was found that the hydrophobic silicone (Coltene President Jet Lightbody) has a water absorption of 0.12%. The hydrophilized silicone (Coltene President Plus Jet Lightbody) absorbed 0.40% water, this corresponded to an increase around 3.3 times that of the hydrophobic silicone. A hydrophilized silicone with an extremely deep wetting angle absorbed 1.13% water, this corresponded to 9.4 times that of the hydrophobic silicone. A particular disadvantage of increased water absorption is the formation of hydrogen gas, which is triggered in the case of silicones by the crosslinker component. The formation of the hydrogen gas leads to bubbles in the model. Finally, the delayed setting of silicones hydro-philized to such an extent is also a disadvantage, since removal of the impression prior to the end of the hardening reaction can possibly deform the impression. Also, the setting thereof is inhibited by latex gloves, which for reasons of hygiene are indispensable in dental treatment.

SUMMARY OF THE INVENTION

It is the object of the invention to provide an impression composition which does not have the disadvantages described above, and which in particular possesses a satisfactory dimensional stability on repeated disinfection, i.e., a satisfactorily small water absorption, and as low and unchanged of a wetting angle as is possible.

The above object is achieved by a rubber-elastic composition which comprises a vulcanizable polyether material which contains, in a completely vulcanized and completely polymerized form, 0.1 to 15 wt. %, relative to the total weight of the composition, of at least one hydrophilic nature imparting agent (hydrophilizing agent) which is selected from the group consisting of hydrophilic silicone oils containing one or more siloxane groups as a hydrophobic part and one or more ether groupings as a hydrophilic part, fluorinated hydrocarbons, block copolymers of ethylene oxide/propylene oxide, fatty alcohol derivatives, alkyl phenol derivatives, fatty amines, amine oxides, fatty acid glycol and glycerin derivatives, fatty acids and fatty acid monoesters.

Surprisingly, it was found that the hydrophilicity of the vulcanizates based on polyether can be improved significantly through the addition of at least one of the hydrophilic nature imparting agents listed above and that they have a low wetting angle. However, the compositions according to the invention either display no increase in water absorption, or only display an insignificant increase water absorption— which is harmless to their use in the dental field. Moreover, their swelling and dimensional change is either non-existent or small, and therefore they distinguish themselves through increased accuracy of reproduction. The above described advantages are particularly surprising in view of the previously known experiences with hydrophilized silicone impression compositions.

It is also completely unexpected that the small wetting angle achieved through the additive according to the invention is retained even after repeated disinfection in an aqueous disinfection bath. Furthermore, it is a surprising advantage that the hydrophilicity of the mixed, but still not vulcanized compositions, can be significantly improved through the additive according to the invention and that they can have a small wetting angle.

Finally, it is of particular advantage that the addition of suitable hydrophilizing agents according to the invention do not have a detrimental effect on the processing and setting time of the compositions, or on the setting transition and other physical values of the compositions (e.g., storage-stability).

DETAILED DESCRIPTION OF THE INVENTION

The following Detailed description is provided as an aid to those desiring to practice the present invention. It is not to be construed as limiting to the present invention, however, since those of ordinary skill in the art will recognize that the embodiments discussed herein (including the Examples provided) may often be easily modified or changed without departing from the spirit or scope of the present inventive discovery. Accordingly, the present invention is only to be limited by the scope of the claims appended hereto including the equivalents thereto.

The rubber-elastic compositions according to the invention generally comprise the following components therein:

(a) a polymerizate or a copolymerizate which comprises at least one vulcanizable polyether;

(b) a polymerization catalyst usual for polyethers (see for example U.S. Pat. No. 4,167,618), activators, accelerators, retarders and stabilizers, which is optionally dissolved or suspended in a solvent or plasticizers usual for them;

(c) at least one hydrophilic nature imparting agent of the type described herein; and (d) optionally other usual plasticizers, solvents, suspension auxiliaries, pyrogenic or precipitated silicic acids, other usual fillers, disinfectant and other usual additives.

The term "vulcanizable polyether material" as used herein is understood to refer to materials with polyether centers and reactive groups which can preferably be present at the end and/or also in the center of the polyether.

Polyglycol ethers have proved to be particularly successful for the production of the starting material. Coming under consideration are, e.g., polymerizates and mixed polymerizates of cyclic ethers, particularly with 3 to 5 ring members, such as ethylene oxide, propylene oxide, tetrahydrofuran, oxethane (trimethylene oxide), and substitution products. In addition to unbranched products, slightly branched products or branched products also come under consideration, such as oxyethylation products of tri- or poly-hydric alcohols.

The polyether center can however also contain an aromatically unsaturated heterocyclic or cycloaliphatic ring, or can also be a siloxane-substituted polyether.

All of the given types of polyglycol ethers can be provided with reactive groups in secondary reactions, by initially introducing substituents which are then able to react with suitable derivative donating reactive groups.

The term "reactive end-groups" as used herein is understood to refer to functional groups which, after suitable initiation by initiators, lead to polymerization of the compositions. Exemplary groups include the following: aziridino groups (DE-B-17 45 810) which have proven particularly successful; as have alkenyl groups (DE-A1-38 587, EP-A2-0 366 977); polyorganosiloxane groups with H—Si groups in the molecule (DE-A1-37 41 575); mercapto groups (EP-A2-0 366 977), acrylic or methacrylic groups (EP-A2-0 173 085); epoxide groups, isocyanate groups and hydroxyl groups. This list is not intended to include all possible reactive groups.

Particularly preferred for the purposes according to the invention are impression materials which are based on polyethers described in DE-B-17 45 810. Preferred initiators for these materials are described in DE-A1-25 15 593 and suitable retarders in EP-A1-0 110 429. Particularly preferred, however, are also the polyether compositions of DE-A1-38 587 which are based on polyethers with vinyl and/or allyl end-groups and a Si—H component. The polyether compositions of DE-A1-37 41 575 are likewise preferred.

In order to prevent a premature hardening of the impression compositions, the polyether materials on the one hand and the catalysts on the other hand must be kept separate from each other until the intended use thereof (the only exceptions to this provision are lightcuring polyether compositions). Both components are preferably present in the form of pastes.

The vulcanizable polyether materials of the one paste can contain identical or chemically similar plasticizers or solvents for improving mixing behavior with the polymerization catalyst of the other paste dissolved in the solvent or plasticizer, or held in suspension by means of suspension auxiliaries or in emulsion by means of emulsifiers.

The use of solutions of the crosslinking agent in suitable plasticizers, solvents or plasticizers is often expedient; since in this way, not only are extreme mixing conditions avoided, but also solid initiators are dissolved.

To avoid the disadvantage of readily mobile crosslinking or hardening agents, these can also be brought into a suitable viscous form, e.g., by adding plastic, such as polyvinyl acetate, or through incorporation of fillers with a large surface, such as a highly-disperse silicic acid.

Usual plasticizers are often satisfactorily compatible with the polyether materials. Their use is advisable not only for economic reasons, but also for improving the compositions properties, particularly for avoiding or reducing crystallization. Phthalic acid esters, glycol derivatives, as well as polymeric softeners, sorbitol esters, etc. are for example suitable. Usual and suitable plasticizers are for example described in Polyethers, Part I, published by Norman G. Gaylord, Interscience Publishers (1963).

The properties of the end-products can be varied to a large extent through the choice of a suitable starting material, with the result that the mechanical values of the end-products can almost be adjusted according to requirements. The addition of larger quantities of plasticizers and/or other usual additives can however influence the water absorption, swelling and change in dimension to an extent such that the impression is unusable. The compositions according to the invention contain, in the completely vulcanized and fully polymerized form, 0.1 to 15, preferably 0.3 to 10 and especially 0.5 to 5 wt. %, relative to the total weight of the compositions, of at least one hydrophilic nature imparting agent which is selected from the group consisting of hydrophilic silicone oils containing one or more siloxane groups as a hydrophobic part and one or more ether groupings as a hydrophilic part, fluorinated hydrocarbons, ethylene oxide/propylene oxide block copolymers, fatty alcohol derivatives, alkyl phenol derivatives, fatty amines, amino oxides, fatty acid glycol and glycerin derivatives, fatty acids and fatty acid monoesters.

These hydrophilic nature imparting agents are either added to the polyether base paste or the catalyst paste alone or on a pro-rata basis to the polyether base paste and catalyst paste in the quantities given. The hydrophilicity of the polyether material cannot be improved below 0.1 wt. %, and above 15 wt. % the water absorption is too high.

The hydrophilizing agent is present in a quantity sufficient such that the vulcanized composition has a 10 second wetting angle smaller than 55°. The vulcanized compositions according to the invention preferably have a 10-second wetting angle smaller than 45°, particularly preferably smaller than 35°.

A "hydrophilic nature imparting agent" as used in the present context is understood as a hydrophilizing agent which reduces the wetting angle of a drop of water or aqueous composition (e.g., plaster suspension, saliva solution, disinfection solution, etc.) vis-a-vis the polyether composition and therefore brings about better wettability of the polyether composition by the liquid. For the definition of the wetting agent, reference is made to Walter Noll, Chemistry and Technology of Silicones, Academic Press, 1968, particularly pages 447 to 452.

As already mentioned above, the wetting angle (also called the contact angle), is the angle at which the edge of a water drop forms relative to the substrate surface. With hydrophobic substrates this angle is above 100° in some cases. The more hydrophilic the substrate, the flatter the shape of the drop becomes and thus the smaller the wetting angle.

The wetting angle is measured using a scanning microscope at the lying droplet 10 seconds after applying a droplet of a saturated solution of calcium sulphate dihydrate at 23° C., 30 minutes after the start of mixing. The 10-second value for the contact angle is methodically advantageous as the influence of evaporation phenomena does not occur. Evaporation would cause a misleading change in the wetting angle, i.e. a reduction. The measuring process is essentially carried out according to the method described in the paper by Bader and Setz, Wettability and Reproduction Accuracy of Modelling Compositions (Dtsch. Zahndrztl. Z. 46, 346–348 (1991).

Suitable hydrophilizing agents which are selected from the group of hydrophilic silicone oils, contain one or more siloxane groups as a hydrophobic part and one or more ether groupings as a hydrophilic part. These ether groupings are preferably ethylenoxy or propylenoxy groups, but may also be, e.g., hydroxyalkyl-substituted ethylenoxy groups. These alkylenoxy groups can be chemically bound to the siloxane group either by way of a carbon atom or also via an oxygen atom. Such hydrophilic silicone oils are described in U.S. Pat. Nos. 3,505,377, 3,980,688 and 4,431,789, and in Union Carbide information on SILWET products. Preferred substances are the types SILWET L-77, SILWET L-7604, SILWET L7001, SILWET L-7600 and SILWET L-7602 given therein. Other representatives of these hydrophilic silicone oils can be found in the product information from the Olin Corporation (SILFAC Products) and in U.S. Pat. Nos. 4,160,776, 4,226,794 and 4,337,168. Suitable hydrophilizing agents from the group of fluorinated hydrocarbon compounds are for example those described in U.S. Pat. No. 2,915,544. Other representatives of this group are F-alkyl-2-ethyl-thiopolyethylene glycol ethoxylates of varying ethylene oxide (EO) numbers.

Hydrophilizing agents suitable according to the invention are also the block copolymers of propylene oxide and ethylene oxide, such as derivatives of propylene glycol and of ethylene diamine which are marketed by Wyandotte under the names PLURONICS and TETRONICS. Ethoxylated polypropylene oxides of different chain lengths are also obtainable as SYNPERONIC types.

Another group of suitable hydrophilizing agents are the fatty alcohol derivatives, particularly the ethoxylated fatty alcohol derivatives, such as fatty alcohol polyglycol ethers, lauryl alcohol and tallow fatty alcohol ethoxylates, octadecanoloxyethylate, dodecanol-, tetradecanol-oxyethylate with various EO proportions. Trimethyl nonanol ethoxylates are also suitable.

Suitable hydrophilizing agents also come from the group of alkyl phenol derivatives, particularly ethoxylated alkyl phenols, such as nonyl phenol polyglycol ethers (e.g., nonyl phenol with 3 to 14 EO), octyl phenol and polyoxyethylene nonyl phenol ethoxylates.

From the group of the fatty amines, the ethoxylated fatty amines are preferred, e.g., fatty amine ethoxylates.

Other suitable hydrophilizing agents are the fatty acid glycol and glycerin derivatives, fatty acids and fatty acid monoesters. The ethoxylated fatty acids and their oleic acids polyglycol esters, coconut fatty acid monoglyceride polyglycol ethers, tallow fatty acid monoglyceride polyglycol ethers are preferred. Other preferred representatives are fatty acid esters such as polyethylene glycol distearate, glycerin monostearate, 2-ethylhexyl palmirate, butyl stearate, isobutyl stearate, isodecyl stearate, isopropyl oleate.

Other suitable hydrophilizing agents are also amine oxides such as lauryl dimethyl amine oxide and stearyl dimethyl amine oxide.

Particularly preferred as hydrophilizing agents are fatty alcohol alkoxylates, in particular fatty alcohol ethoxylates. The alkoxylated fatty alcohols and acylated alkoxylated fatty alcohols are straight- and branched-chain alcohols with C10 to C16, which are reacted with 2 to 10 mol alkylene oxide and then optionally reacted with a C2 to C4 monocarboxylic acid. Also, particularly preferred are the alkoxylated silicone derivatives and the block copolymers of propylene oxide/ethylene oxide, which are referred to and/or described herein.

The suitable hydrophilizing agents are not limited to the HLB values given in the examples (see definition for HLB below). Other special examples of the hydrophilizing agents usable according to the invention are for example described in the "Index of Non-Ionic Surfactants" by Bernard Parant, 1988 and in Ullman's Encyklopädie der technischen Chemie, Volume 22, 4th edition, 1982.

The vulcanizable polyether materials according to the invention are particularly suitable for the purposes of taking dental impressions. However, they are also suitable as doubling materials and impression compositions for technical and medicinal purposes, e.g. in orthopaedics for taking impressions of the fermur cavity prior to hip joint endoprosthetics. The following examples serve to explain the invention. The invention is not limited to the examples.

EXAMPLES

The wetting angle is measured with a G1/G40 contact angle measuring system (Kruss). The wetting angle measuring device G1 permits precise reproduction of drop profiles on solids surfaces. The G40 measuring system includes a video tube with beam splitter, with the result that simultaneous observation of a drop through the goniometer eyepiece (drop size) and the video camera (digital pictorial evaluation) is made possible.

Measurement is carried out on the lying drop at 23° C. and 50% relative atmospheric humidity. Thirty (30) minutes after the start of mixing of the compositions, a drop, which is always the same size, of a calcium sulphate hydrate solution saturated at 23° C., is deposited onto the elastomer cured to a smooth surface between glass plates and measurement is started immediately. The 10-second value is used for the evaluation.

The results in the comparison are summarized in Tables 1 to 3.

The water absorption is determined using a rectangular plate (l=38 mm, w=32 mm, h=3 mm) with 28.5 cm$^2$ wettable surface. 60 minutes after the start of mixing the vulcanizate is weighed (measured value a) and left in distilled water at 23° C. for 20 hours. Immediately after removal, the testpiece is dried on the surface and weighed again (measured value b). The percentage water absorption is calculated according to the formula % absorption=[(b−a)/a]×100

The water-retaining capacity was determined by weighing the testpiece again (measured value c) after storing the testpiece for a further 2 hours in air at 50 % relative atmospheric humidity at 23° C. The water-retaining capacity in % is calculated according to the formula % residue=[(c−a)/a]×100

The dimensional change was measured on the basis of ADA (American Dental Association) 19 at 100% relative atmospheric humidity after 20 hours.

The results of the comparison are set forth in detail in Table 1.

The dipping-bath disinfections are carried out according to the instructions for use provided by the manufacturer in commercially available disinfection solutions. 10 minutes' residence time are used per disinfection process for IMPRE-SEPT (ESPE), likewise 10 minutes for BANICIDE (Pascal), but 20 minutes for COECIDE XL PLUS (GC America).

The results of the comparison are set forth in detailed in Table 3.

Used as hydrophilizing agents in the examples are the following non-ionogenic surfactants:

PLURONIC block copolymer surfactants (BASF Wyandotte),

SILWET polyalkylene oxide polymethyl siloxanes (Union Carbide Corp.),

REWOPAL fatty alcohol polyalkylene oxide methyl ether (REWO),

ANTAROX nonyl phenol ethoxylates (Rhone-Poulenc), and

FLUORAD fluorinated surfactants (3M).

Reference is made in the following Examples to the respective HLB value of the surfactants. The term HLB value (hydrophilic lipophilic balance) is to be understood as a measure of the hydrophilicity and lipophilicity of nonionogenic surfactants. The HLB value can be determined both experimentally as well as through calculation processes in certain cases. In general, the numerical values lie between 1 and 20, in rare cases even above this (up to 40). Substances with a low HLB value (say below 10) are generally good water/oil emulsifiers, while the more hydrophilic surfactants with a higher HLB value act as oil/water emulsifiers. The behavior of other surfactants can thus be deduced from the knowledge of the HLB value.

Example 1 (Comparative Example)

46.6 g of an aziridino polyether which was obtained according to Example 12 of DE-B-17 45 810 are mixed with 21.5 g of dibenzyl toluene, 9.64 g hydrogenated palm oil and 22.3 g kieselguhr. In this way 100 g of a paste A are obtained. 33.4 g dibenzyl toluene, 15.6 g 2,5-dichlorobenzene sulphonic acid methyl ester, 15.1 g polyisobutylene, 10.0 g pyrogenic silicic acid and 25.9 g kieselguhr are also kneaded to give 100 g of 15 a paste B.

The two pastes are fully mixed together in the weight ratio 4 A:1 B. After a few minutes a rubber-elastic composition is obtained. 30 minutes after preparation, the wetting angle is determined as 64°. The water absorption is 1.05%, the waterretaining capacity 0.18%, the change in dimension +/−0.00%.

Example 2

100 g of paste A are kneaded as in Example 1 with the addition of 0.5 g of a block copolymer surfactant comprising propylene oxide and ethylene oxide with an average molar mass of 3800 (HLB=1.0) (PLURONIC L 101), and mixed with paste B from Example 1 in the weight ratio 4 A:1 B. After a few minutes a rubber-elastic composition is obtained. 30 minutes after preparation the wetting angle is determined as 49°.

Example 3

100 g of paste A are kneaded as in Example 1 with the addition of 0.5 g polyalkylene oxide polymethyl siloxane, molar mass 600 (HLB=5–8) (SILWET L-77) and mixed with paste B from Example 1 in the weight ratio 4 A:1 B. After a few minutes a rubber-elastic composition is obtained. 30 minutes after preparation the wetting angle is determined as 34°.

Repeating the contact angle measurement after 7 months' storage time (at 23° C.) gives a wetting angle of 33°. This shows that the wetting angle has remained unchanged and the composition according to the invention has a very good storage-stability.

Example 4 (Comparative Example)

60.10 g of an aziridino polyether which was obtained according to Example 12 of DE-B-17 45 810 are mixed with 3.2 g Normulgen, 10.7 g of a block copolymer surfactant comprising propylene oxide and ethylene oxide with an average molar mass of 6500 (HLB=15.0) (PLURONIC P 105), 16.0 g of a block copolymer surfactant comprising propylene oxide and ethylene oxide with an average molar mass of 4400 (HLB=0.5) (PLURONIC L 121), 2.1 g Telamide, 7.5 g hydrogenated palm oil and 17.9 g kieselguhr. In this way 117.5 g c)f a paste C are obtained. 40 g of this paste C are thoroughly mixed with 10 g of the paste B from Example 1. After a few minutes a rubber-elastic composition is obtained. 30 minutes after preparation the wetting angle is determined as 18°. The water absorption is 10.05%, the water-retaining capacity 7.,40%, the change in dimension+ 0.94%.

Example 5

100 g of a paste A according to Example 1 are produced. 32.7 g of a sulphonium salt which was obtained according to Example 31 of DE-C-25 15 593, 22.2 g acetyl tributyl citrate, 5.8 g of a block copolymer surfactant comprising propylene oxide and ethylene oxide with an average molar mass of 6500 (HLB=15.5) (PLURONIC P 105), 10.1 g pyrogenic silicic acid, 28.5 g kieselguhr and 0.7 g pigments are also kneaded to a total 100 g of a paste D. The two pastes are thoroughly mixed in the weight ratio 7 A:1 D. After a few minutes a rubber-elastic composition is obtained. 30 minutes after preparation the wetting angle is determined as 51°. The water absorption is 1.15%, the water-retaining capacity 0.20%, the change in dimension 0.00%. After 10 minutes' disinfection of a testpiece in a disinfection dipping bath (IMPRESEPT, ESPE), then rinsing under cold water and 2 hours' storage in air at 23° C. and 50% relative atmospheric humidity, the wetting angle is determined as 52°.

Examples 6 to 23

100 g of the paste A according to Example 1 are kneaded with the quantity x of hydrophilizing agent given below in each case to give a hydrophilized paste Ax. In this way 100+x g of a paste Ax are obtained. 100 g of a paste D are also prepared as described in Example 5. The two pastes are thoroughly mixed together in the weight ratio 7 Ax:1 D. After a few minutes a rubber-elastic composition is obtained. 30 minutes after preparation the wetting angle is determined. The measured values for the 10-second wetting angle are detailed in Table 2.

Example 6

100 g of A+5.17 g of fatty alcohol polyalkylene oxide methylether (coconut fat section) (REWOPAL MT 2540). 30 minutes after preparation the wetting angle is determined as 28°. The water absorption is 1.48%, the water-retaining capacity 0.43%, the change in dimension+0.08%.

Example 7

100 g of A+1.96 g of a block copolymer surfactant comprising propylene oxide and ethylene oxide with an average molar mass of 3800 (HLB=1.0) (PLURONIC L 101). 30 minutes after preparation, the wetting angle is determined as 22°. The water absorption is 1.57%, the water-retaining capacity 0.51%, the change in dimension+0.14%.

Example 8

100 g of A+1.44 g of a block copolymer surfactant comprising propylene oxide and ethylene oxide with an average molar mass of 6500 (HLB=15.0) (PLURONIC P 105).

Example 9

100 g of A+5.17 g of a block copolymer surfactant comprising propylene oxide and ethylene oxide with an average molar mass of 2200 (HLB=16.0) (PLURONIC L 44).

Example 10

100 g of A+5.17 g of a block copolymer surfactant comprising propylene oxide and ethylene oxide with an average molar mass of 2900 (HLB=15.0) (PLURONIC L 64).

Example 11

100 g of A+1 g of a nonyl phenol ethoxylate with 9 EO units (HLB=13.0) (ANTAROX CO-630).

Example 12

100 g of A+1 g of a polyalkylene oxide polymethyl siloxane with EO/PO units, molar mass 20000, methoxy terminated (HLB=9–12) (SILWET L-7001).

Example 13

100 g of A+1 g of a polyalkylene oxide polymethyl siloxane with EO units, molar mass 4000 (HLB=13–17) (SILWET L-7604).

Example 14

100 g of A+1 g of a fatty alcohol polyalkylene oxide methylether (REWOPAL MT 5722).

Example 15

100 g of A+5 g of a block copolymer surfactant comprising propylene oxide and ethylene oxide with an average molar mass of 4150 (HLB=16.5) (PLURONIC P 75).

Example 16

100 g of A+1 g of a fluorinated alkyl alkoxylate (FLUORAD FC-430).

Example 17

100 g A+1 g of a fluorinated alkyl ester (Fluorad FC-430).

Example 18

1 00 g of A+1 g of a nonyl phenol ethoxylate with 4 EO groups (HLB=8.8) (ANTAROX CO-430).

Example 19

1 g of the catalyst solution which was obtained according to Example 3 of DE-A1-38 587 is mixed with 200 g of a diallyl ether of a polypropylene glycol with an average molecular weight of 2000 and 2 g palladium on calcium carbonate and 90 g silanised pyrogenic silicic acid. In this way 292 g of a catalyst paste are obtained.

64 g of the diallyl ether described above are also kneaded with 47 g of a reaction product, prepared according to Example 2 of the aforementioned publication, comprising tetramethyl cyclotetrasiloxane and 4,4-bis-(allyloxy)-2,2-diphenyl propane and 190 g calcium carbonate, coated with stearic acid. In this way 301 g of a base paste are obtained.

The catalyst paste and base paste are mixed together thoroughly in equal parts by weight. After a few minutes a rubber-elastic composition is obtained. 30 minutes after preparation, the wetting angle is determined as 66°.

Example 20

100 g of a catalyst paste which was prepared as described in Example 19 are mixed with 0.5 g of a polyalkylene oxide polymethyl siloxane of molar mass 600 (HLB=5–8) (SIL-WET L-77).

100 g of a base paste, which was prepared as described in Example 19, are also kneaded with 0.5 g of the same polyalkylene oxide polymethyl siloxane. The two pastes are mixed together in the weight ratio 1:1. After a few minutes, a rubber-elastic composition is obtained. 30 minutes after preparation, the wetting angle is determined as 35°.

Example 21

100 g of a catalyst paste which was prepared as described in Example 19 are mixed with 0.5 g of a fatty alcohol polyalkylene oxide methyl ether (REWOPAL MT 5722).

100 g of a base paste which was prepared as described in Example 19 are also kneaded with 0.5 g of the same surfactant.

The two pastes are mixed together in the weight ratio 1:1. After a few minutes, a rubber-elastic composition is obtained. 30 minutes after preparation, the wetting angle is determined as 47°.

Example 22

100.0 g of a polypropylene glycol urethane methacrylate which was obtained according to Example 1 of EP-A3-0 173 085 are mixed with 0.5 g 2,4,6-trimethyl benzoyl diphenylphosphine oxide to give a homogeneous solution. The transparent solution thus obtained is poured into a mould, covered with a glass plate and lit by means of a standard commercial light apparatus (DELO-Lux) for 5 minutes. A thoroughly hardened rubber-elastic composition with a dry surface is obtained. 30 minutes after preparation the wetting angle is determined as 61°.

Example 23

100 g of a polypropylene glycol urethane methacrylate, which was obtained according to Example 1 of EP-A3-0 173 085, are mixed with 0.5 g 2,4,4-trimethyl benzoyl diphenyl phosphine oxide and 2.0 g of a block copolymer surfactant comprising propylene oxide and ethylene oxide with an average molar mass of 3830 (HLB=1.0) (PLURONIC L 101) to give a homogeneous composition of 102.5 g. The transparent solution thus obtained is poured into a mould, covered with a glass plate and lit using a standard commercial light apparatus (DELO-Lux) for 5 minutes. A thoroughly hardened rubber-elastic composition with a dry surface is obtained. 30 minutes after preparation, the wetting angle is determined as 32°.

Example 24

Testpieces are prepared from the polyether composition according to Example 5 for determining the dimensional stability according to ADA 19. The change in dimension according to ADA 19 is determined after 1 hour as –0.10%, after 24 hours as –0.24%. The 10-second wetting angle is 51°. These testpieces are then placed in a freshly prepared commercial disinfectant solution (COECIDE XL PLUS, GC America) and left for 20 minutes in this solution at 23° C. according to the manufacturer's instructions. Subsequently, the testpieces are rinsed briefly under running cold water and dried for 2 hours in air at 23° C. and 50% relative atmospheric humidity. This procedure is then repeated twice so that the testpieces have undergone a triple disinfection. After the last disinfection, the change in dimension and the wetting angle are determined again. The change in dimension is +0.05%, the wetting angle is determined as 52°. This experiment shows that the polyether composition according to the invention can be disinfected 3 times and the wetting angle and dimensional stability retained.

Example 25

Testpieces are prepared from the polyether composition according to Example 7 for determining the dimensional stability according to ADA 19. The change in dimension according to ADA 19 is determined after one hour as –0.15% and after 24 hours as 0.25%. The 10-second wetting angle is 22°. These testpieces are then placed in a freshly prepared commercial disinfection solution (BANICIDE, Pascal) and left for 10 minutes in this solution at 23° C. according to the manufacturer's instructions. Subsequently, the testpieces are rinsed briefly under running cold water and dried for 2 hours in air at 23° C. and 50% relative atmospheric humidity. This procedure is then repeated twice so that the testpieces have undergone a triple disinfection. After the last disinfection, the change in dimension and the wetting angle are again determined. The change in dimension is +0.15%, the wetting angle is determined as 23°. This experiment shows that the polyether composition according to the invention can be disinfected three times and the wetting angle and dimensional stability retained.

Example 26

Two standard commercial hydrophilized addition-crosslinking silicone impression compositions, IMPRINT (3M) and REPROSIL (Dentsply) are disinfected in direct comparison to the compositions 2, 3, 5 and 7 according to the invention in a commercial dipping bath customary in the trade (IMPRESEPT, ESPE) and the influence of the disinfection process on the wetting angle of the impression compositions is checked. For this, testpieces of all the impression compositions are prepared and 30 minutes after mixing their 10-second wetting angle is determined prior to disinfection (Table 3). The testpieces are then left in the standard commercial disinfection dipping bath for 10 minutes. The testpieces are then rinsed briefly under running cold water and left to dry for 2 hours in air at 23° C. and 50% relative humidity. Afterwards, the 10-second wetting angle is determined again after disinfection. The result in Table 3 shows that the hydrophilized silicones according to the state of the art experience a significant increase in the wetting angle after only one disinfection and therefore clearly suffer a loss of wettability in the subsequent impression process with plaster suspension. In contrast, the compositions according to the invention show no or only a slight change in wetting angle and 25 have a wettability which remains good even after disinfection.

TABLE 1

Influence of type/content of hydrophilizing agent on wetting angle, water absorption and loss and the change in dimension.

| Example | Hydrophilizing agent | Content (in % of the total) composition | 10-sec WA | Water absorption, % | Change in dimension, % |
|---|---|---|---|---|---|
| 1 (Comparative example) | — | 0 | 64° | 1.05 | 0.18 ± 0.00 |
| 4 (Comparative example) | Block copolymer surfactant | 18.18 | 18° | 10.05 | 7.40 ± 0.94 |
| 5 (according to the invention) | Block copolymer surfactant | 0.73 | 51° | 1.15 | 0.20 ± 0.00 |
| 6 (according to the invention) | Fatty alcohol poly-alkylene oxide methyl ether | 5.03 | 28° | 1.48 | 0.43 ± 0.08 |
| 7 (according to the invention) | Block copolymer surfactant | 2.41 | 22° | 1.57 | 0.51 ± 0.14 |

TABLE 2

Influence of type/content of hydrophilizing agent on the wetting angle.

| Example | Hydrophilizing agent | Content in % | 10-sec WA |
|---|---|---|---|
| 1 (Comparative example) | — | 0 | 64° |
| 2 (according to the invention) | Block copolymer surfactant | 0.40 | 49° |
| 3 (according to the invention) | Polyalkylene oxide polymethyl siloxane | 0.40 | 34° |
| 4 (Comparative example) | Block copolymer surfactant | 18.18 | 18° |
| 5 (according to the invention) | Block copolymer surfactant | 0.73 | 51° |
| 6 (according to the invention) | Fatty alcohol poly-alkylene oxide methyl ether | 5.03 | 28° |
| 7 (according to the invention) | Block copolymer surfactant | 2.41 | 22° |
| 8 (according to the invention) | Block copolymer surfactant | 1.97 | 40° |
| 9 (according to the invention) | Block copolymer surfactant | 5.03 | 30° |
| 10 (according to the invention) | Block copolymer surfactant | 5.03 | 25° |
| 11 (according to the invention) | nonyl phenol ethoxylate | 1.59 | 26° |
| 12 (according to the invention) | Polyalkylene oxide polymethyl siloxane | 1.59 | 35° |
| 13 (according to the invention) | Polyalkylene oxide polymethyl siloxane | 1.59 | 44° |
| 14 (according to the invention) | Fatty alcohol poly-alkylene oxide methyl ether | 1.59 | 25° |
| 15 (according to the invention) | Block copolymer surfactant | 4.89 | 30° |
| 16 (according to the invention) | Fluorinated alkyl alkoxylate | 1.59 | 42° |
| 17 (according to the invention) | Fluorinated alkyl ester | 1.59 | 42° |
| 18 (according to the invention) | Nonyl phenol ethoxylate | 1.59 | 53° |
| 19 (Comparative example) | — | 0 | 66° |
| 20 (according to the invention) | Polyalkylene oxide polymethyl siloxane | 0.50 | 35° |
| 21 (according to the invention) | Fatty alcohol poly-alkylene oxide methyl ether | 0.50 | 47° |
| 22 (Comparative example) | — | 0 | 61° |
| 23 (according to the invention) | Block copolymer surfactant | 1.95 | 32° |

TABLE 3

Behavior of hydrophilized silicone and polyether impression compositions on disinfection.

| Impression composition | Composition | 10-sec WA before disinfection | 10-sec WA after disinfection | % increase in WA |
|---|---|---|---|---|
| Imprint, 3M | USP 86022442 WO 87/03001 | 55° | 75° | 36 |
| Reprosil Dentsply | EP-B1-0 231 420 | 45° | 65° | 44 |
| Example 2 | | 49° | 49° | 0 |
| Example 3 | | 34° | 36° | 6 |
| Example 5 | | 51° | 52° | 2 |
| Example 7 | | 22° | 22° | 0 |

We claim:

1. A rubber-elastic composition, comprising a vulcanizable polyether material,
   wherein the vulcanizable polyether material is selected from the group consisting of:
   a polyether having an aziridino group,
   a polyether having a vinyl end-group and a Si—H component,
   a polyether having an allyl end-group and a Si—H component, and
   a polyether having both a vinyl and an allyl end-group and a Si—H component;
   said composition containing in the completely vulcanized and completely polymerized form, 0.1 to 15 wt. %, relative to the total weight of the composition, of at least one hydrophilic nature imparting agent that is selected from the group consisting of:
   a hydrophilic silicone oil having one or more siloxane groups as a hydrophobic part and one or more ether groups as a hydrophilic part,
   a fluorinated hydrocarbon,
   a block copolymer of ethylene oxide/propylene oxide containing hydroxyl end groups,
   a fatty alcohol derivative selected from the group consisting of C10 to C16 straight and branched chain alcohols that are reacted with an alkylene oxide in a mole ratio of 1:2 to 1:10 and then optionally methylated or reacted with a C2 to C4 monocarboxylic acid,
   an ethoxylated alkyl phenol,
   an ethoxylated fatty amine, and
   an amine oxide; and
   said composition having in the completely vulcanized and completely polymerized form a 10-second wetting angle of less than 55°.

2. The rubber-elastic composition of claim 1, containing in the completely vulcanized and completely polymerized form, relative to the total weight of the composition, 0.2 to 10 wt. %, relative to the total weight of the composition, of the hydrophilic nature imparting agent.

3. The rubber-elastic composition of claim 1, containing in the completely vulcanized and completely polymerized form, relative to the total weight of the composition, 0.5 to 5 wt. %, relative to the total weight of the composition, of the hydrophilic nature imparting agent.

4. The rubber-elastic composition of claim 1, wherein the composition in the completely vulcanized and completely polymerized form has a 10-second wetting angle of less than 45°.

5. The rubber-elastic composition of claim 1, wherein the composition in the completely vulcanized and completely polymerized form has a 10-second wetting angle of less than 35°.

6. The rubber-elastic composition of claim 1, wherein the composition in the completely vulcanized and completely polymerized form, after two 10- to 20-minute disinfections in an aqueous disinfection solution, has a 10-sec wetting angle of less than 55°.

7. The rubber-elastic composition of claim 1, wherein the composition in the completely vulcanized and completely polymerized form, after two 10- to 20-minute disinfections in an aqueous disinfection solution, has a 10-sec wetting angle of less than 45°.

8. The rubber-elastic composition of claim 1, wherein the composition in the completely vulcanized and completely polymerized form, after two 10- to 20-minute disinfections in an aqueous disinfection solution, has a 10-sec wetting angle of less than 35°.

9. The rubber-elastic composition of claim 1, wherein the hydrophilic nature imparting agent is said hydrophilic silicone oil.

10. The rubber-elastic composition of claim 1, wherein the hydrophilic nature imparting agent is said fatty alcohol derivative.

11. The rubber-elastic composition of claim 1, wherein the hydrophilic nature imparting agent is said block copolymer of propylene oxide and ethylene oxide.

12. In a method of forming a model of teeth or mucous membranes wherein a modeling impression is formed of the teeth or the mucous membrane, the improvement comprising:
    forming a modeling impression with a modeling composition that comprises a vulcanizable polyether material,
    wherein the vulcanizable polyether material is selected from the group consisting of:
    a polyether having an aziridino group,
    a polyether having a vinyl end-group and a Si—H component,
    a polyether having an allyl end-group and a Si—H component, and
    a polyether having both a vinyl and an allyl end-group and a Si—H component;
    said composition containing in the completely vulcanized and completely polymerized form, 0.1 to 15 wt. %, relative to the total weight of the composition, of at least one hydrophilic nature imparting agent that is selected from the group consisting of:
    a hydrophilic silicone oil having one or more siloxane groups as a hydrophobic part and one or more ether groups as a hydrophilic part,
    a fluorinated hydrocarbon,
    a block copolymer of ethylene oxide/propylene oxide containing hydroxyl end groups,
    a fatty alcohol derivative selected from the group consisting of C10 to C16 straight and branched chain alcohols that are reacted with an alkylene oxide in a mole ratio of 1:2 to 1:10 and then optionally methylated or reacted with a C2 to C4 monocarboxylic acid,
    an ethoxylated alkyl phenol,
    an ethoxylated fatty amine, and
    an amine oxide;
    provided that said composition possesses in the completely vulcanized and completely polymerized form a 10-second wetting angle of less than 55°.

13. A process for preparing a ready-to-use polyether impression modeling composition that contains the following ingredients:
    (a) a vulcanizable polyether material,
    wherein the vulcanizable polyether material is selected from the group consisting of:
    a polyether having an aziridino group,
    a polyether having a vinyl end-group and a Si—H component,
    a polyether having an allyl end-group and a Si—H component, and
    a polyether having both a vinyl and an allyl end-group and a Si—H component;
    (b) a polymerization catalyst for polyethers,
    (c) at least one hydrophilic nature imparting agent selected from the group consisting of:

a hydrophilic silicone oil having one or more siloxane groups as a hydrophobic part and one or more ether groups as a hydrophilic part, a fluorinated hydrocarbon, a block copolymer of ethylene oxide/propylene oxide containing hydroxyl end groups, an ethoxylated alkyl phenol, an ethoxylated fatty amine, an amine oxide, and a fatty alcohol derivative selected from the group consisting of C10 to C16 straight and branched chain alcohols that are reacted with an alkylene oxide at a mole ratio of 1:2 to 1:10 and then optionally methylated or reacted with a C2 to C4 monocarboxylic acid;

(d) optionally an activator, an accelerator, a retarder and a stabilizer, (e) optionally a solvent or a plasticizer, and (f) optionally a pyrogenic or precipitated silicic acid, a filler, and a disinfectant;

the method comprising the steps of:

producing a base paste A by mixing optionally partial quantities of constituents (a) and (c) to (f);

producing a catalyst paste B by mixing optionally partial quantities of constituents (b) to (f); and producing a ready-to-use impression composition by mixing equivalent quantities of said base paste A and said catalyst paste B together;

provided that said composition possesses in the completely vulcanized and completely polymerized form a 10-second wetting angle of less than 55°.

14. The method of claim 12, wherein the hydrophilic nature imparting agent is said block copolymer of propylene oxide and ethylene oxide.

15. The process of claim 13, wherein the hydrophilic nature imparting agent is said block copolymer of propylene oxide and ethylene oxide.

* * * * *